United States Patent [19]

Morgan et al.

[11] Patent Number: 4,913,654
[45] Date of Patent: Apr. 3, 1990

[54] SHIELD FOR ORTHODONTIC APPLIANCE

[76] Inventors: Timothy J. Morgan, 1611 Kent Ave.; Patrick E. O'Neal, 1124 Klondike Rd., both of Quincy, Ill. 62301

[21] Appl. No.: 215,287

[22] Filed: Jul. 5, 1988

[51] Int. Cl.⁴ .............................................. A61C 3/00
[52] U.S. Cl. ...................................... 433/8; 433/11; 433/15
[58] Field of Search .................. 433/8, 9, 10, 11, 12, 433/13, 14, 15, 16

[56] References Cited

U.S. PATENT DOCUMENTS

| | | | |
|---|---|---|---|
| 4,180,912 | 1/1980 | Kesling | 433/8 |
| 4,355,975 | 10/1982 | Fujita | 433/11 |
| 4,512,740 | 4/1985 | Kurz | 433/22 |
| 4,527,975 | 7/1985 | Ghafari et al. | 433/8 |
| 4,687,441 | 8/1987 | Klepacki | 433/8 |
| 4,712,999 | 12/1987 | Rosenberg | 433/8 |

FOREIGN PATENT DOCUMENTS

| | | | |
|---|---|---|---|
| 2903768 | 8/1980 | Fed. Rep. of Germany | 433/11 |
| 3504822 | 8/1986 | Fed. Rep. of Germany | 433/10 |

Primary Examiner—John J. Wilson
Attorney, Agent, or Firm—Joseph W. Holloway

[57] ABSTRACT

A plastic shield removably attached to an orthodontic appliance comprising a pliable C-shaped strip having projecting legs which flex outwardly over the appliance when the strip is pressed digitally thereagainst. The legs carry one or more longitudinally extending ridges which cam over the appliance and are thereafter biased against the brackets or the ligatures of the appliance in the manner of a flexural clamp or detent.

12 Claims, 2 Drawing Sheets

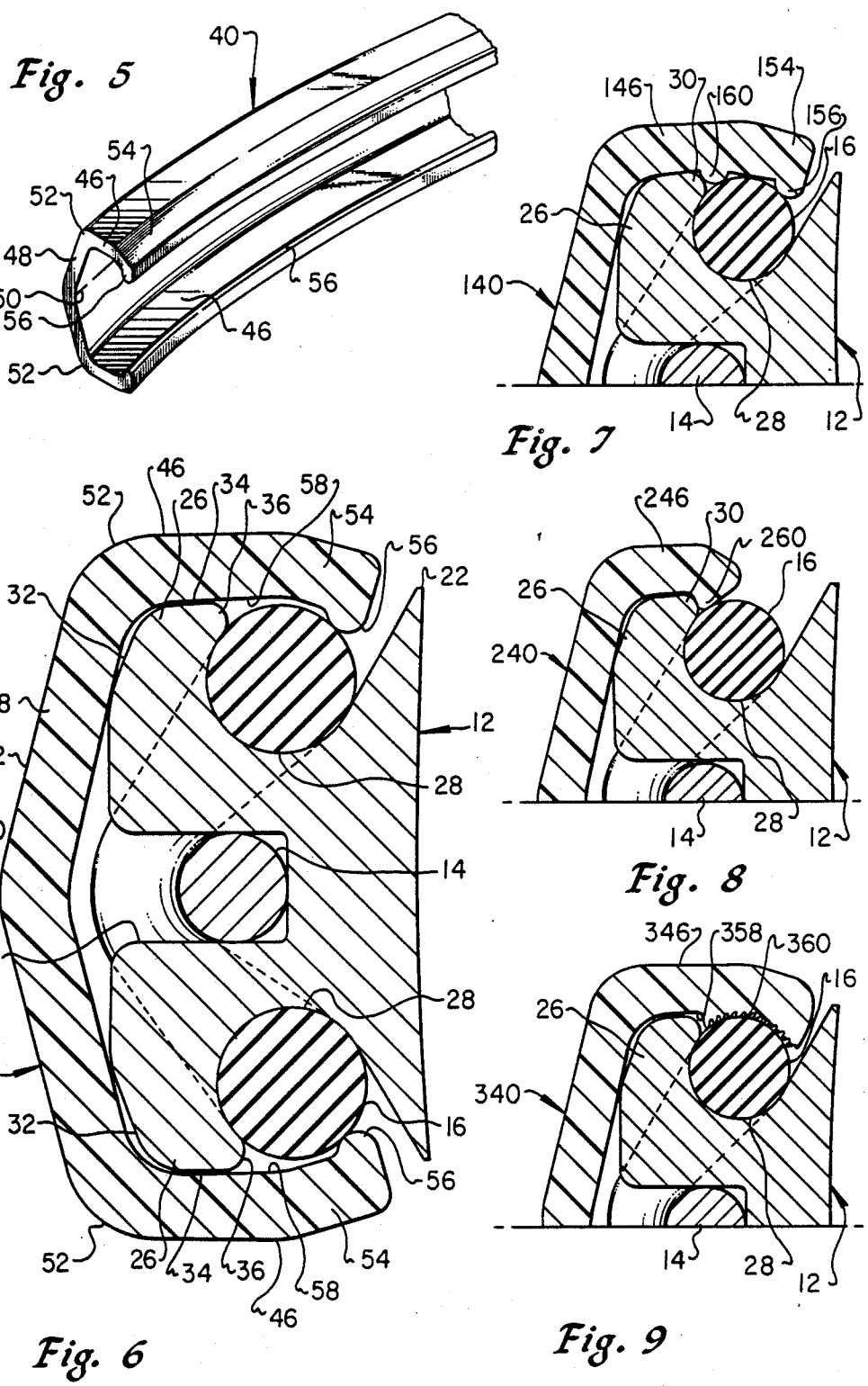

SHIELD FOR ORTHODONTIC APPLIANCE

BACKGROUND OF THE INVENTION

A well-known type of orthodontic appliance includes a plurality of brackets cemented to the labial surfaces of a number of the patient's teeth. The brackets are individually attached to an arch wire by elastomeric rings, wires or other such ligature means. Such components of common orthodontic appliances exhibit surface irregularities and pinch points which may rapidly traumatize the lip and cheek tissues overlying the appliance particularly after initial installation of the appliance in the mouth and following periodic adjustments of the appliance during the course of treatment.

This problem was recognized in Craven H. Kurz U.S. Pat. No. 4,512,740 issued Apr. 23, 1985. According to Kurz, a plastic shield placed frontally over an appliance would obviate irritation and soreness of the inner tissues of the cheeks and lips caused by rubbing against sharp appliance elements. Kurz discloses a shield which comprises an elongated arcuate member having a smooth labial surface and a plurality of lingually extending fingers which curve around the arch wire to position the shield in place in overlying relation to the brackets. However, in his specification, Kurz recognizes the need for supplementary means for securing his shield to the appliance. To this end, Kurz suggests that dental floss be threaded between the interproximal spaces of the teeth and tied to the shield to assure that it will remain in place over the appliance. This lack of positive attachment of the Kurz shield to elements of an appliance greatly reduces the utility and effectiveness of this shield construction. Thus, the task of tying the shield to the appliance must be repeated each time the patient cleans food particles from his teeth and the appliance after eating. Not only is this a substantial inconvenience and time-consuming activity, but the perserverance required to thread the floss between the teeth and to secure the thread about the shield and appliance would likely deter youngsters and other less determined patients from removing and reinstalling the shield as needed to maintain proper oral hygiene.

Not only do the fingers of Kurz inherently fail to provide positive and reliable shield attachment, but the fixed spacing between adjacent fingers of Kurz may or may not coincide with the intervals between a patient's brackets to permit each and every finger to engage the arch wire. Misalignment of any finger with an exposed arch wire segment would cause that finger to bear awkwardly upon a bracket and exacerbate Kurz's attachment problem. Therefore, it follows that use of fingers or other projecting attachment means with a shield of the Kurz type would require either customized patient fitting or provision of an impractical number of finger arrangements to accommodate the limitless variations in the size and shape of orthodontic appliances.

Another type of protective orthodontic shield known as "Hug Caps" is offered to orthodontists by Kreative Koncepts, Inc. of Hinsdale, Ill. This device is intended to cover completely the frontal portion of an individual bracket. Each shield comprises an elastomeric ring to which is attached an elastic cap which covers an underlying bracket to provide a smooth labial surface. The ring itself engages the bracket in a well-known manner serving as the actual ligature for securing the arch wire to the bracket. Individual caps are installed as needed on brackets by the use of a hemostat or like instrument. The manufacturer advises that special care be employed to avoid puncture of the cap membrane as the ligature ring is drawn over and about the brackets. The "Hug Caps" product has two principal drawbacks:

1. This device is intended to be installed by an orthodontist, not by the patient himself; therefore, office instruments and professional skill must be utilized to assure proper ligature installation and to avoid accidental damage to the shield and detachment or bending of the brackets.

2. It is likely that oral detritus will enter between the brackets and overlying cap membranes and that a serious oral hygiene problem will develop unless the caps are periodically removed to permit thorough cleaning of the caps and brackets. Such shield removal and subsequent reinstallation would require the patient to visit his orthodontist and incur an additional expense for the sole purpose of cleaning this type of shield. A. Kieth Amstutz et al U.S. Pat. No. 4,559,013 issued Dec. 17, 1985, points out the deficiencies of various prior art shields such as chamois or cloth inserted between the teeth and lip tissue, pliable wax strips pressed around braces to smooth over sharp edges and expensive thermoplastic protectors formed over the patient's teeth. Amstutz proposes an oral shield molded of silicone which covers completely the teeth and an attached orthodontic appliance wherein the molded indentations in the shield interfit with the teeth and the appliance to maintain the shield in place. The original expense involved in molding a shield about an individual patient's teeth and appliance remains a substantial deterrent to widespread use of custom fitted shields. Since Amstutz relies entirely on the interfit of the molded shield indentations with the appliance elements to secure the shield in place, it follows that a costly new shield might be required each time an appliance is substantially adjusted during the course of orthodontic treatment.

SUMMARY OF THE INVENTION

The general object of this invention is to provide a protective orthodontic shield which is structurally modified to obviate the deficiencies of prior art devices presently used for this purpose.

A principal object is to provide a shield strip comprising an open, C-shaped channel which exhibits inherent flexural clamping ability for reliably retaining the strip in position on an orthodontic appliance. The shield may advantageously consist of resilient plastic material permitting the open channel to be snapped over the appliance for interfering engagement with the brackets or the elastomeric ligature rings on each tooth. Contrary to the requirements of the "Hug Caps" shield, for example, installation of a shield according to this invention requires only that the user press or smooth the strip against the appliance elements; and, removal is quickly and safely accomplished by grasping one end of the strip and peeling the shield from the appliance.

Another important object is to provide a protective shield strip which is well-adapted to interfit securely with metal or plastic brackets and elastomeric o-ring type ligatures of various sizes and shapes and with brackets which tilt at varying angles to the teeth and the archwire. A closely related object is to avoid the high cost involved in custom molding a shield for individual patients as proposed by Amstutz, for example.

A practical commercial object is achieved by continuously extruding or molding the shield according to this invention in coils as long as required to obtain optimum production efficiency. Subsequently the strip can be cut and packaged for over-the-counter sale in convenient lengths or in smaller coils. It becomes a simple matter for the customer-user to cut off the correct length of shield strip needed to cover his entire appliance or at least that part thereof which causes irritation and soreness. Due to the simple construction of the strip shield and resulting low manufacturing cost and selling price, there is little incentive to attempt to clean and store a strip for reuse; therefore, the hygienic problems encountered in the reusable shields of Kurz, Kreative Koncepts and Amstutz are obviated.

These and other features and objects of this invention and the manner of obtaining them will become apparent and the invention will be more fully understood by having reference to the following detailed description of embodiments of the invention taken in conjunction with the accompanying drawings.

BRIEF DESCRIPTION OF THE DRAWINGS

FIG. 5 is a fragmental isometric view of an orthodontic shield strip constructed according to this invention;

FIG. 6 is an enlarged view of a transverse section taken along lines 6—6 of FIG. 2;

FIG. 7 is a partial section similar to FIG. 6 showing a first modification of the shield;

FIG. 8 is a partial section similar to FIG. 6 showing a second modification of the shield; and, FIG. 9 is a partial section similar to FIG. 6 showing a third modification of the shield.

DETAILED DESCRIPTION OF PREFERRED EMBODIMENTS

The drawings depict a portion of a typical orthodontic appliance, indicated generally by numeral 10, essentially comprising a bracket 12, and arch wire 14 and an elastomeric o-ring 16 which serves as a ligature to secure the arch wire to the bracket. Since the structure and operation of this so-called light wire appliance do not constitute part of the present invention, the structural features of the appliance will be described only to the extent required to facilitate an understanding of the inventive aspects of the orthodontic shield described and claimed herein.

Figure 3:
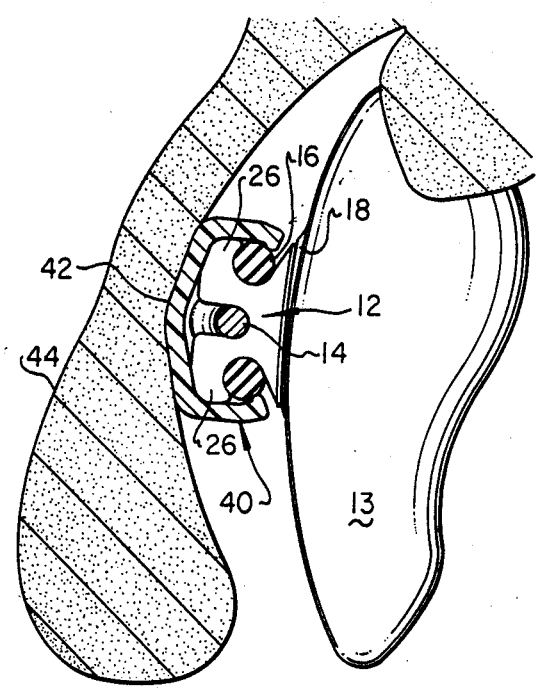
FIG. 3 is a partial transverse sectional view taken generally along lines 3—3 of FIG. 2 which illustrates the shield of this invention in relation to the appliance and to a wearer's tooth and lip.

The brackets 12 may be made of stainless steel or a suitably rigid plastic material and are bonded to the labial surface of the patient's teeth 13 by a thin layer of cement 18, as shown in FIG. 3. A bracket is cemented to each tooth in a position and at an angular attitude adapted to produce movement of the teeth in response to forces applied by the arch wire 14 to the brackets 12. The course of such treatment may last several months during which time the elements of the appliance may be relocated, adjusted and changed in size and shape. The bracket 12 has a pair of identical standards 20 which project labially or forwardly from a common base plate 22 in laterally spaced relation to one another. Transverse arch wire slots 24 extend medially of the standards and open labially therefrom. The slots 24 effectively bifurcate the distal portions of the standards forming oppositely extending arms 26 which are relieved to form generally semi-cylindrical grooves 28.

Figure 1:
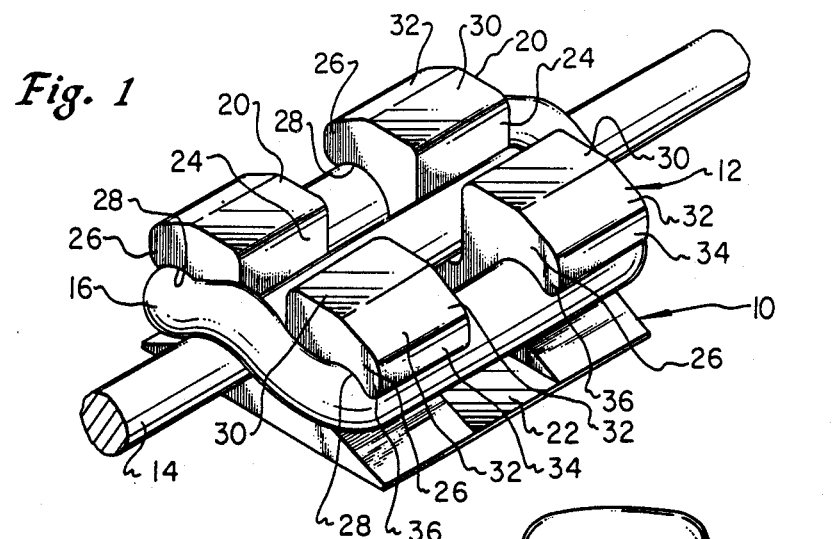
FIG. 1 is an isometric view of the bracket, arch wire and ligature components of one type of orthodontic appliance to which the present invention relates.
Figure 2:
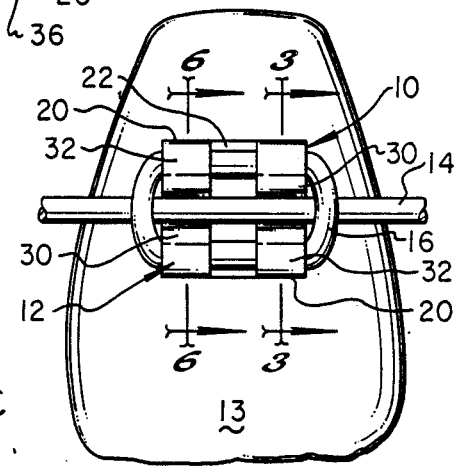
FIG. 2 is a front elevational view of a single anterior tooth having a bracket of the type shown in FIG. 1 cemented to its labial surface.
Figure 4:
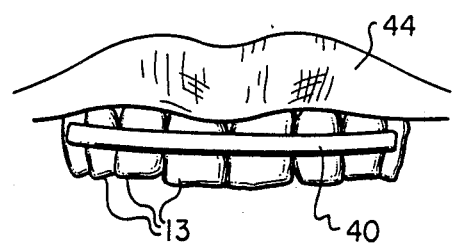
FIG. 4 is a front elevational view of a shield installed over an orthodontic appliance attached to the upper anterior teeth of a wearer.

The arch wire 14, shown in the drawings, is round in cross section; however, square or rectangular wire is commonly used by orthodontists to obtain desired variations in the torquing and angulating coaction of the wire 14 and bracket 12. It will be understood that the arch wire coacts with each of several tooth-mounted brackets which together constitute the appliance and that such an appliance may be fabricated to treat any number of teeth. FIG. 4, for example, illustrates a common application of an orthodontic appliance in which a patient's six upper anterior teeth are treated. The arch wire 14 is laid transversly in the aligned slots 24 of the standards 20 wherein the arch wire is powerfully held against the slot bottoms and sides by the elastic o-ring 16. As best illustrated in FIG. 1, the o-ring 16 is adapted to surround the bracket 12 tightly in overlying engagement with the arch wire 14. The grooves 28 underlying the arms 26 receive and retain an o-ring which, in turn, fixes the arch wire to the bracket. As best illustrated in FIG. 1, the standards have intersecting labial surfaces 30 and 32 and the arms 26 terminate distally in surfaces 34. Arcuate tips 36 provide transitional surfaces connecting the surfaces 34 and the semi-cylindrical groove surfaces 28.

Turning now to the advantageous features of the protective orthodontic shield which is the subject of this invention and which is indicated in the drawings in its entirety by numeral 40, FIG. 3 shows a preferred embodiment of the shield attached to the appliance to overlie the same and present a smooth labial surface 42 which is in intimate contact with the tender tissue inside the wearer's upper lip 44. FIG. 5 shows that the shield 40 comprises a strip of generally rectangular, C-shaped channel wherein the lingual or rearward opening between the projecting legs 46 of the channel is opposite to an upright back wall 48 of the channel which provides the smooth labial surface 42. The back wall 48 projects forwardly or labially at its midpoint to form a longitudinally extending peak 50, the purpose of which will hereinafter become apparent. The legs 46 are generally normal to the back 48 wall and are integrally joined thereto by curved transitional segments 52. The legs 46 terminate in reentrant segments 54 which, in the embodiment of the invention shown in FIGS. 3, 5 and 6, have generally semicircular ridges 56 which project inwardly from an interior wall surface 58 toward the longitudinal centerline of the channel-like shield 40 and extend the full length of the channel strip.

In the embodiments of the invention shown in FIGS. 7, 8 and 9, only the structural details of the legs 46 of the hereinbefore described shield 40 have been modified. In the FIG. 7 embodiment, supplemental semicircular ridges 160 extend inwardly from leg 146 in labially spaced relation to the ridges 156. In the FIG. 8 embodiment, the legs 246 of the shield 240 are shortened and terminate in hook-like ridges 260. The FIG. 9 embodiment displays a shield 340 wherein multiple serrations 360 are formed in an arcuate section of the walls 358 of the legs 346.

From the foregoing description of the various embodiments of the invention, it will be appreciated by those familiar with plastic extrusion and continuous molding processes that the cross sectional configurations of all the described shields lend themselves to these processes for economically fabricating the shields in strips or coils of any desire length. Moreover, many low cost thermoplastic materials are well-suited for these processes and likewise provide a material having excellent properties for this application. One such material comprises a polymeric organic compound such as polyvinyl chloride (PVC). It is preferrable that the fabricated strip be clear, have a durometer value of 80 to 90, and that the thickness of the back channel wall 48 and the channel legs 46 be between 0.015 and 0.020 inches It is essential that the selected channel material be sufficiently pliable that, when its lingual side is pressed against an appliance, the legs 46 will spread apart and cam over the appliance as hereinafter described.

OPERATION OF THE INVENTION

After obtaining a quantity of shield material either in precut strips or in a small coil, the user can easily detach a length of shield strip sufficient to cover all or a portion of his orthodontic appliance. A prepared strip is held in the user's fingers in alignment with the appliance with the lingual opening of the channel 40 facing the appliance as if the channel shown in FIG. 6 were detached and moved to the left of the bracket 12 with the ridges 56 just in contact with the surfaces 32 of one or more of the brackets comprising the appliance. The user then presses against the shield opposite each bracket of his appliance, or he may simply digitally wipe the entire outer shield surface 42, to attach the shield to the brackets generally as depicted in FIG. 4. Slight digital pressure applied to the medial longitudinal peak 50 of the surface 42 will cause the channel back wall 48 to flex inwardly whereby the attached legs 46 will spread apart sufficiently to allow the ridges 56 to slide or cam over the surfaces 32 and 34 on the four arms 26 of the bracket standards 20. As continued pressure is applied to the shield, the fully installed position of the shield relative to the appliance will be quickly and simply achieved whereby the ridges 56 will override the exposed outer surface of the o-ring 16 to an extent limited by bearing contact between the back wall 48 of the channel 40 and the frontal surface of the bracket 12. During shield installation, the reentrant segments 54 of legs 46 are also flexed or cammed outwardly from the channel's longitudinal centerline to the extent required for these segments and the semicircular ridges 56 to override the o-ring 16 on each bracket.

From the foregoing explanation it will be understood that the shield 40 may be digitally pressed over the brackets and o-ring ligatures and essentially snapped into place whereby a releasable detent effect occurs between the ridges 56 and the o-rings 16. Such detent effect is achieved by correct selection of the dimensions of the channel relative to the dimensions of the bracket and o-ring and by the provision of hinge-like flexural areas occurring generally along the medial peak 50 of the channel back wall 48 and along the line of reentrance of the leg portion 54. The span between the opposed ridges 56 of a channel 40 in the unflexed condition, shown in FIG. 5, is somewhat less than that when the ridges are held apart by bearing contact on the o-ring 16, as shown in FIG. 6. Such spreading of the ridges 56 about a medial hinge line 50 extending longitudinally along the channel wall 48 elastically deforms this wall and results in the ridges being biased into clamping engagement with the o-ring 16. A similar flexural hinge action occurs at the juncture of the legs 46 and their reentrent terminal segments 54. The elasticity of the legs 46 creates an inwardly directed, reactive bias as a result of the legs being cammed outwardly to allow the opposed ridges 56 to slide over the cylindrical outer surface of the o-ring 16. Such biasing force urges the ridges into interferring and clamping engagement with the o-ring whereby the shield is held on the brackets by a releasable detent effect.

It is believed that some elastic deformation of the o-ring itself will occur as the ridges 56 cam thereover and that both the resulting pressure acting against the ridges and mutual surface deformation assist in securing the shield 40 to the appliance brackets 12.

As best shown in FIG. 5, the radius of the semicylindrical ridges 56 is selected to allow bearing contact with the o-ring surface with slight clearance between the inner walls 58 of the legs 46 and the bracket surfaces 34, thereby insuring that the latter do not hold the ridges away from the o-ring. Preferably, the reach between the interior surface of the back wall 48 of the channel 40 and the ridges 56 will be just sufficient to permit resilient clamping of each bracket and o-ring therebetween, in the manner shown in the upper portion of FIG. 6. However, due to tooth-to-tooth variations in the tilt and projection of brackets, the shield wall 48 may be slightly spaced from the front of the bracket, as shown in the lower portion of FIG. 6. Nevertheless, due to the thinness of the channel wall 48 and legs 46 and the pliable nature of the channel material, the shield will deform quite readily to permit the shield to snap onto those adjacent brackets which display substantial misalignment from one another.

Since a shield constructed in accordance with this disclosure is held thereon by a resilient detent effect, the shield may be quickly and easily removed by simply grasping the same and stripping it from the appliance.

The alternate embodiments of the invention operate somewhat differently from the FIGS. 5 and 6 embodiment, principally in the specific manner and means for securing the legs of the channel to the appliance elements. In the FIG. 7 embodiment, ridges 156 and like shaped supplemental ridges 160 coact to receive the o-ring 16 therebetween in wedging engagement; and, the second ridges 160 are firmly seated between the arcuate arm tips 30 and the o-ring. The coaction of the shield 140 with the bracket 12 and o-ring 16 is essentially the same as that described above with respect to shield 40, however, the supplemental ridges 160 are cammed into biased engagement with both the o-ring 16 and the bracket when shield 140 is pressed onto the appliance, whereby additional gripping contact and wedging action are provided.

FIG. 8 discloses an embodiment wherein the o-ring is not engaged by ridges projecting from the leg of the channel 240. Instead, hook-like ridges are adapted to cam over the bracket standards 26 and to snap inwardly over and seat behind the arcuate tips 30 of the bracket arms 26. This modification is well-suited for applications of the shield 240 where the o-ring 16 is extremely firm or where wire rather than an elastomeric ring is used as a ligature means for securing the arch wire 14 to the brackets 12.

Finally, the FIG. 9 embodiment comprehends a modified shield 340 wherein serrations 360 relieved in the inwardly facing wall 358 of the legs 346 are biased against the contiguous surface of the o-ring. Each of the projecting ridges formed by the serrations is urged by the resilient legs 346 into contact with the o-ring whereby the total surface-to-surface gripping engagement between the ridges and the o-ring is substantially increased over that displayed in the FIG. 6 or FIG. 7 embodiments.

The foregoing description of the embodiments of the invention shown in the drawings is illustrative and explanatory only; and, various changes in the size, shape and materials, as well as in specific details of the illustrated construction may be made without departing from the scope of the invention. Therefore, we do not intend to be limited to the details shown and described herein, but intend to cover all changes and modifications which are encompassed by the scope and spirit of the appended claims.

For example, the dimensions of the disclosed channels 40, 140, 240 and 340 and the arrangement of the legs and ridges thereof can be modified to provide the advantages of a snap-on/detent action when the shield is applied to orthodontic appliances having different components or components of substantially different sizes and shapes.

Although a shield made of clear PVC substantially masks the visibility of the appliance, it may be desirable from an aesthetic standpoint to make the shield of tooth-colored material for users who are self-conscious about wearing an orthodontic appliance which detracts from facial appearance.

What we claim as our invention is:

1. A protective shield for covering orthodontic appliance elements including brackets, an arch wire and elastomeric ligature rings, wherein said shield comprehends:
    a flexible strip having an upstanding wall and projecting legs defining a C-shaped channel;
    said wall having a smooth outer surface facing labially;
    said legs projecting lingually and defining an opening extending longitudinally therebetween;
    said wall having a medial longitudinal flexural hinge whereby said legs are elastically spreadable for receiving said elements in said opening interiorly of said channel; said legs having means for detenting engagement with said ligature rings; and
    said legs are thereafter elastically biased together for detenting engagement with said rings.

2. The shield defined in claim 1, wherein: said legs carry longitudinal projections for detenting engagement with said rings.

3. The shield defined in claim 2, wherein: said projections comprise semicircular ridges extending longitudinally of said legs.

4. The shield define in claim 1, wherein: said legs include reentant terminal segments elastically spreadable for receiving said elements whereby said segments are thereafter elastically biased together for detenting engagement with said rings.

5. The shield defined in claim 4, wherein: said segments carry longitudinally extending ridges for detenting engagement with said rings.

6. The shield defined in claim 4, wherein: first and second longitudinal ridges extend from said segments for detenting engagement with a portion of each of said rings positioned therebetween.

7. A protective shield for covering orthodontic appliance elements including brackets, an arch wire and elastomeric ligature rings, wherein said shield comprehends:
    a flexible strip having an upstanding wall and projecting legs defining a C-shaped channel;
    said wall having a smooth outer surface facing labially;
    said legs projecting lingually and defining an opening extending longitudinally therebetween; said legs having means for detenting engagement with said ligature rings; and,
    said wall and said legs are elastically deformed and said legs are biased together to engage said rings therebetween when said elements are in said channel.

8. The shield defined in claim 7, wherein: said legs have longitudinally extending means for detenting engagement with said rings for releasably securing said shield to said appliance.

9. A protective strip readily attachable and removable with respect to a plurality of labially extending ligature elements of an orthodontic appliance, including:
    an elongated, C-shaped strip of flexible material;
    said strip including a longitudinally extending wall having a smooth labial surface;
    said wall having a pair of longitudinally extending legs projecting therefrom and defining a lingually facing opening therebetween;
    each of said legs having at least one longitudinally extending ridge projecting therefrom; and,
    said ligature elements being received in said opening, and said ridges on said legs being biased for detenting engagement with said ligature elements when said strip is attached to said appliance.

10. The protective strip defined in claim 9, wherein: each of said legs has plural longitudinally extending ridges projecting therefrom.

11. The improvement defined in claim 9, wherein: said wall has a medial peak providing a flexural hinge longitudinally along said wall.

12. In a protective shield removably attachable to a labially-extending element of an orthodontic appliance, the improvement comprising:
    a C-shaped strip of flexible material;
    said strip including a longitudinally extending wall having a smooth labial surface;
    said wall having a pair of longitudinally extending legs projecting therefrom and defining a lingually facing opening therebetween;
    said legs including longitudinally extending arcuate surfaces having multiple serrations formed thereon and projecting toward said opening; and,
    said opening receiving said elements when said shield is attached to said appliance.

* * * * *